US010449022B2

(12) United States Patent
Okai

(10) Patent No.: US 10,449,022 B2
(45) Date of Patent: Oct. 22, 2019

(54) ORAL CARE IMPLEMENT

(71) Applicant: COLGATE-PALMOLIVE COMPANY, New York, NY (US)

(72) Inventor: Takahide Okai, Highland Park, NJ (US)

(73) Assignees: Colgate-Palmolive Company, New York, NY (US); Omron Healthcare Co., Ltd., Kyoto (JP)

( * ) Notice: Subject to any disclaimer, the term of this patent is extended or adjusted under 35 U.S.C. 154(b) by 203 days.

(21) Appl. No.: 15/362,110

(22) Filed: Nov. 28, 2016

(65) Prior Publication Data

US 2017/0151045 A1    Jun. 1, 2017

Related U.S. Application Data

(60) Provisional application No. 62/261,716, filed on Dec. 1, 2015.

(51) Int. Cl.
*A46B 9/02* (2006.01)
*A46B 9/04* (2006.01)
(Continued)

(52) U.S. Cl.
CPC .......... *A61C 17/222* (2013.01); *A46B 5/0095* (2013.01); *A46B 9/02* (2013.01);
(Continued)

(58) Field of Classification Search
CPC .. A46B 9/02; A46B 9/028; A46B 9/04; A46B 9/06
See application file for complete search history.

(56) References Cited

U.S. PATENT DOCUMENTS 6,766,548 B1   7/2004   Lukas et al.
6,920,659 B2   7/2005   Cacka et al.
(Continued)

FOREIGN PATENT DOCUMENTS

JP    2009125080    6/2009
WO    WO2015164486   10/2015

OTHER PUBLICATIONS

Colgate® 360°® Total® Advanced Floss-Tip† Bristles Toothbrush, http://www.colgatetotal.com/toothbrushs/360-floss-tip, date unknown but downloaded from the internet prior to the date of the subject application, 3 pp.
(Continued)

*Primary Examiner* — Randall E Chin

(57) ABSTRACT

An oral care implement having an arrangement of tooth cleaning elements thereon. The oral care implement may include a head extending from a proximal end to a distal end and comprising first and second peripheral sides. A plurality of tooth cleaning elements extend from the head and are arranged in groups including a first peripheral grouping of tooth cleaning elements positioned adjacent the first peripheral side of the head and having first and second types of tooth cleaning elements, a distal grouping of tooth cleaning elements positioned adjacent the distal end of the head and having a third type of tooth cleaning element, and a proximal grouping of tooth cleaning elements positioned adjacent the proximal end of the head and having the third type of tooth cleaning element. The first, second, and third types of tooth cleaning elements are different in at least one more structural characteristics.

17 Claims, 13 Drawing Sheets

(51) Int. Cl.
*A46B 9/06* (2006.01)
*A61C 17/22* (2006.01)
*A46B 5/00* (2006.01)
*A46D 1/00* (2006.01)

(52) U.S. Cl.
CPC .............. *A46B 9/028* (2013.01); *A46B 9/04* (2013.01); *A46B 9/06* (2013.01); *A46D 1/023* (2013.01); *A46D 1/0238* (2013.01); *A46D 1/0276* (2013.01)

(56) References Cited

U.S. PATENT DOCUMENTS

| | | |
|---|---|---|
| D632,894 S | 2/2011 | Shigeno et al. |
| D644,439 S | 9/2011 | Shigeno et al. |
| 8,453,285 B2 | 6/2013 | Dickie |
| D696,029 S | 12/2013 | Seyler |
| D702,946 S | 4/2014 | Shigeno et al. |
| 8,800,091 B2 | 8/2014 | Hohlbein |
| D724,845 S | 3/2015 | Yoshida et al. |
| D734,613 S | 7/2015 | Yoshida et al. |
| 2005/0060822 A1 | 3/2005 | Chenvainu et al. |
| 2006/0026784 A1* | 2/2006 | Moskovich ......... A46B 5/0062 15/110 |
| 2006/0117508 A1* | 6/2006 | Hohlbein ............ A46B 5/002 15/110 |
| 2006/0240380 A1* | 10/2006 | Chenvainu ......... A46B 11/0079 433/80 |
| 2009/0007357 A1* | 1/2009 | Meadows ............ A46B 9/005 15/167.1 |
| 2011/0047736 A1 | 3/2011 | Jimenez et al. |
| 2011/0152909 A1 | 6/2011 | Jimenez et al. |
| 2012/0266397 A1 | 10/2012 | Iwahori |
| 2013/0198980 A1 | 8/2013 | Iwahori et al. |
| 2014/0123414 A1 | 5/2014 | Okazaki |
| 2014/0123423 A1* | 5/2014 | Morgott ............. A46D 1/0207 15/167.1 |
| 2014/0366289 A1 | 12/2014 | Shimoyama et al. |
| 2015/0150367 A1 | 6/2015 | Moskovich et al. |

OTHER PUBLICATIONS

International Search Report and the Written Opinion of the International Searching Authority issued in International Application PCT/US2016/063839 dated Feb. 10, 2017.

* cited by examiner

ORAL CARE IMPLEMENT

CROSS-REFERENCE TO RELATED PATENT APPLICATIONS

This application claims the benefit of priority to U.S. Provisional Patent Application Ser. No. 62/261,716 filed Dec. 1, 2015, the entirety of which is incorporated herein by reference.

BACKGROUND

A toothbrush is used to clean the teeth by removing plaque and debris from the tooth surfaces. In typical oral care implements, bristles are bundled together in a bristle tuft and mounted within tuft holes. While substantial efforts have been made to modify the cleaning elements of toothbrushes to improve the efficiency and effectiveness of the oral cleaning process, the industry continues to pursue arrangements of cleaning elements that will improve upon the existing technology. Therefore, a need exists for an oral care implement having an improved arrangement of tooth cleaning elements.

BRIEF SUMMARY

The present invention may be directed, in one aspect, to an oral care implement having an arrangement of tooth cleaning elements thereon. The oral care implement may include a head extending from a proximal end to a distal end and comprising a first peripheral side and a second peripheral side. A plurality of tooth cleaning elements extend from the head and are arranged in groups including a first peripheral grouping of tooth cleaning elements positioned adjacent the first peripheral side of the head and comprising first and second types of tooth cleaning elements, a distal grouping of tooth cleaning elements positioned adjacent the distal end of the head and including a third type of tooth cleaning element, and a proximal grouping of tooth cleaning elements positioned adjacent the proximal end of the head and including the third type of tooth cleaning element.

In one aspect, the invention may be an oral care implement comprising: a head extending along a longitudinal axis from a proximal end to a distal end, the head comprising a first peripheral side and a second peripheral side opposite the first peripheral side; a plurality of tooth cleaning elements extending from a front surface of the head, the plurality of tooth cleaning elements arranged in a tooth cleaning element field, the tooth cleaning element field comprising: a first peripheral grouping of tooth cleaning elements adjacent the first peripheral side of the head, the first peripheral grouping of tooth cleaning elements comprising a first type of tooth cleaning element and a second type of tooth cleaning element; a distal grouping of tooth cleaning elements adjacent the distal end of the head, the distal grouping of tooth cleaning elements comprising a third type of tooth cleaning element; a proximal grouping of tooth cleaning elements adjacent the proximal end of the head, the proximal grouping of tooth cleaning elements comprising the third type of tooth cleaning element; and a central grouping of tooth cleaning elements located between the distal and proximal groupings of tooth cleaning elements, the central grouping of tooth cleaning elements comprising a fourth type of tooth cleaning element.

In another aspect, the invention may be an oral care implement comprising: a head extending along a longitudinal axis from a proximal end to a distal end, the head comprising a first peripheral side and a second peripheral side opposite the first peripheral side; a plurality of tooth cleaning elements extending from a front surface of the head, the plurality of tooth cleaning elements arranged in a tooth cleaning element field, the tooth cleaning element field comprising: a first peripheral grouping of tooth cleaning elements adjacent the first peripheral side of the head, the first peripheral grouping of tooth cleaning elements comprising tufts of tapered bristles and one or more elastomeric elements; a distal grouping of tooth cleaning elements adjacent the distal end of the head, the distal grouping of tooth cleaning elements comprising tufts of spiral bristles; and a proximal grouping of tooth cleaning elements adjacent the proximal end of the head, the proximal grouping of tooth cleaning elements comprising tufts of spiral bristles.

In yet another aspect, the invention may be an oral care implement comprising: a head extending along a longitudinal axis from a proximal end to a distal end, the head comprising a first peripheral side and a second peripheral side opposite the first peripheral side; a plurality of tooth cleaning elements extending from a front surface of the head, the plurality of tooth cleaning elements arranged in a tooth cleaning element field, the tooth cleaning element field comprising: a first peripheral grouping of tooth cleaning elements adjacent the first peripheral side of the head, the first peripheral grouping of tooth cleaning elements comprising tufts of tapered bristles and one or more elastomeric elements; a distal grouping of tooth cleaning elements adjacent the distal end of the head, the distal grouping of tooth cleaning elements comprising tufts of single component end-rounded bristles; and a proximal grouping of tooth cleaning elements adjacent the proximal end of the head, the proximal grouping of tooth cleaning elements comprising tufts of single component end-rounded bristles.

In a further embodiment, the invention can be a refill head for an electric toothbrush comprising: a head extending along a longitudinal axis from a proximal end to a distal end, the head comprising a first peripheral side and a second peripheral side opposite the first peripheral side; a plurality of tooth cleaning elements extending from a front surface of the head, the plurality of tooth cleaning elements arranged in a tooth cleaning element field, the tooth cleaning element field comprising: a first peripheral grouping of tooth cleaning elements adjacent the first peripheral side of the head, the first peripheral grouping of tooth cleaning elements comprising a first type of tooth cleaning element; a distal grouping of tooth cleaning elements adjacent the distal end of the head, the distal grouping of tooth cleaning elements comprising a second type of tooth cleaning element; a central grouping of tooth cleaning elements located in a central region of the front surface of the head, the central grouping of tooth cleaning elements comprising a third type of tooth cleaning element; and a soft tissue cleanser located on a rear surface of the head, the soft tissue cleanser comprising a plurality of protuberances extending from the rear surface.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
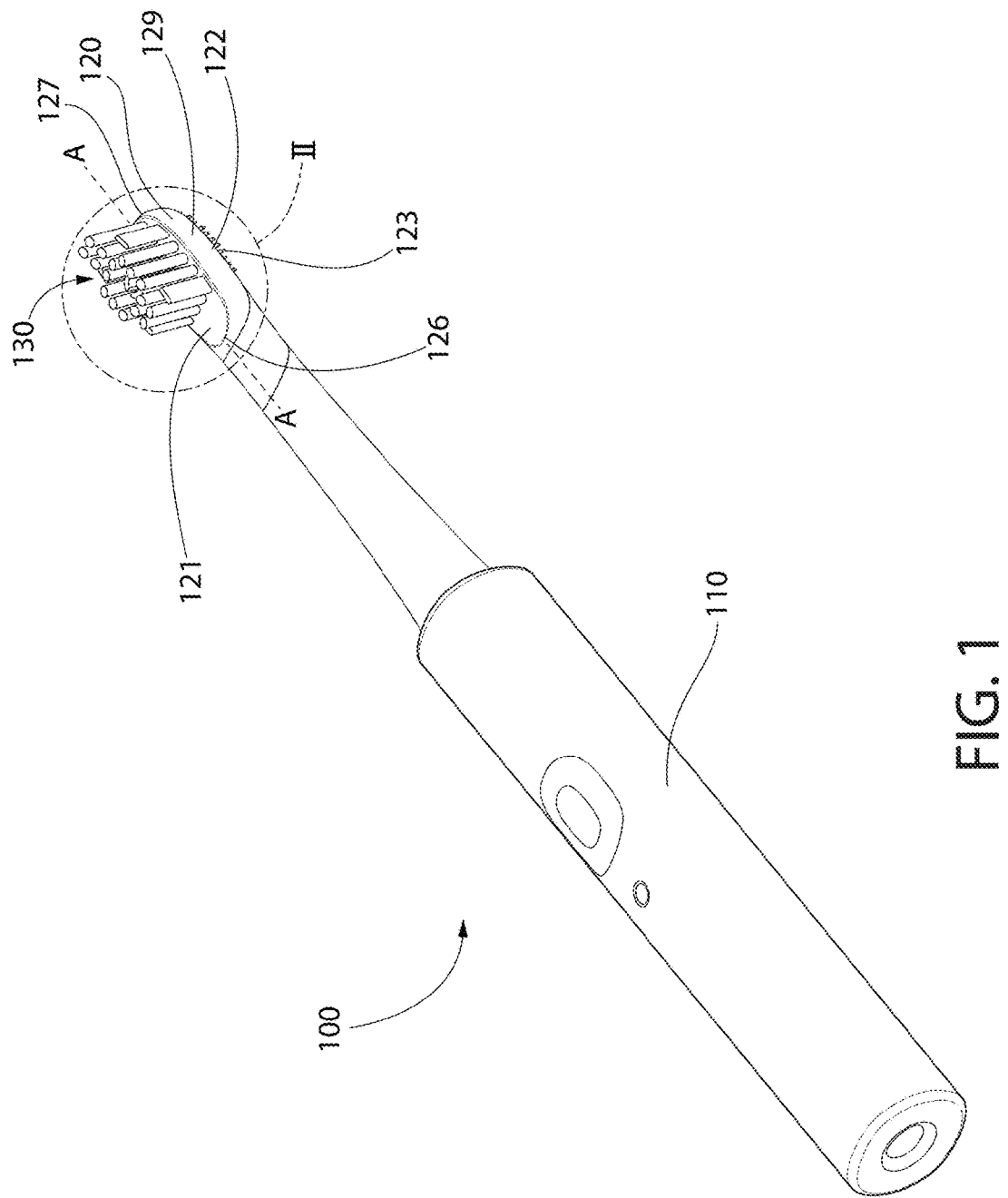
FIG. 1 is perspective view of an oral care implement in accordance with a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Referring to FIG. 1, an oral care implement 100 is illustrated in accordance with an embodiment of the present invention. In the exemplified embodiment, the oral care implement 100 is illustrated as an electric or powered toothbrush. However, the invention is not to be so limited and the disclosure set forth herein is also applicable to a manual toothbrush. In still other embodiments, the oral care implement 100 can take on other forms such as being a tongue scraper, a gum and soft tissue cleanser, a water pick, an interdental device, a tooth polisher, a specially designed ansate implement having tooth engaging elements or any other type of implement that is commonly used for oral care. Thus, it is to be understood that the inventive concepts discussed herein can be applied to any type of oral care implement unless a specific type of oral care implement is specified in the claims.

The oral care implement 100 generally comprises a handle 110 and a head 120. The head 120 may be formed as a part of a refill head that is detachably coupled to a stem of the handle 110. Thus, the head 120 may be detachably coupled to the handle 110 in some embodiments as is standard in the electric toothbrush industry whereby the handles are reused with different refill heads so that the consumer is not required to replace the entire toothbrush including the electronics when the tooth cleaning elements become frayed or damaged and require replacement. In other embodiments, the handle 110 and the head 120 may be integrally formed as a single unitary structure using a molding, milling, machining or other suitable process. In still other embodiments, the handle 110 and the head 120 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners.

The head 120 and the handle 110 are typically formed of a rigid plastic material, such as for example without limitation polymers and copolymers of ethylene, propylene, butadiene, vinyl compounds and polyesters such as polyethylene terephthalate. Of course, the invention is not to be so limited in all embodiments and the handle 110 may include a resilient material, such as a thermoplastic elastomer, as a grip cover that is molded over portions of or the entirety of the handle 110 to enhance the gripability of the handle 110 during use. For example, portions of the handle 110 that are typically gripped by a user's palm during use may be overmolded with a thermoplastic elastomer or other resilient material to further increase comfort to a user during handling of the oral care implement 100.

Figure 7:
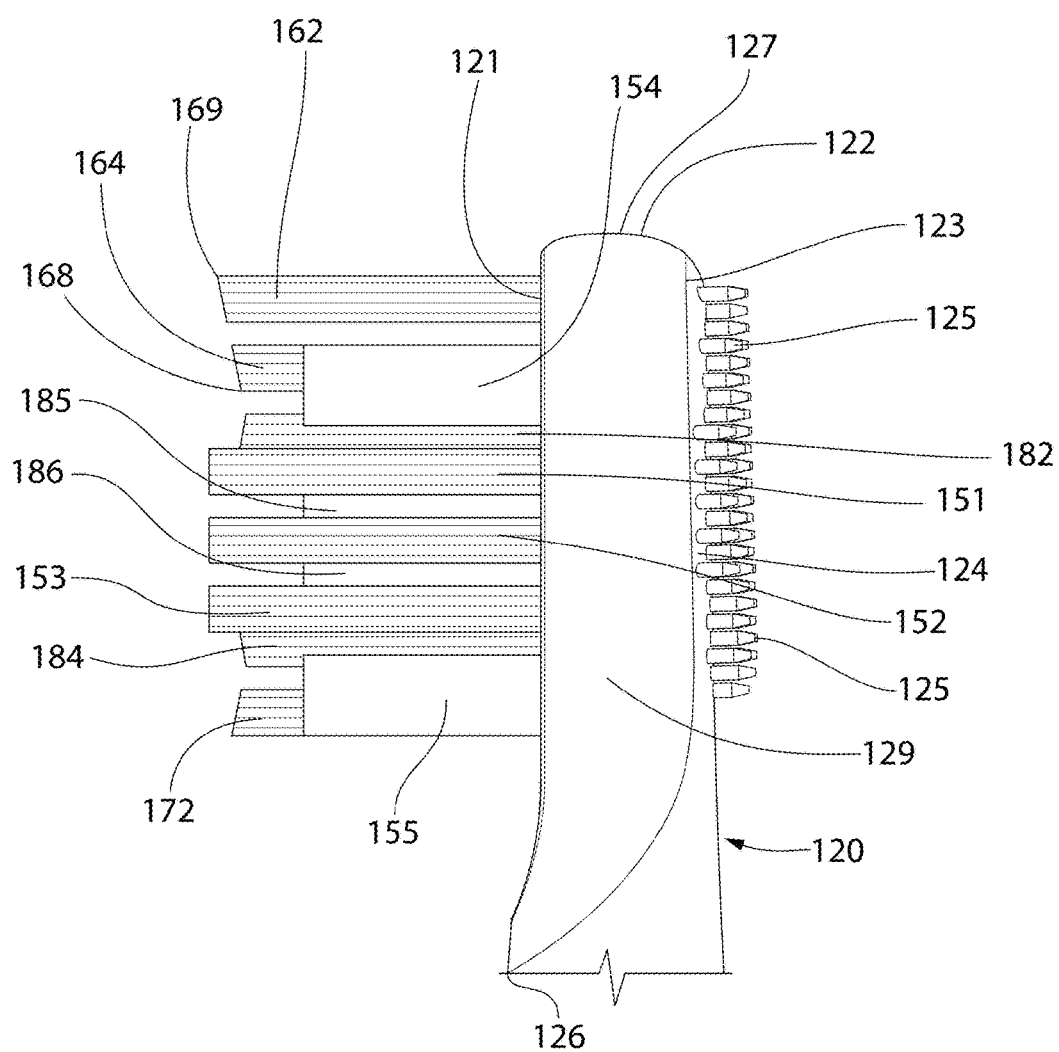
FIG. 7 is a side view of the head of the oral care implement of FIG. 1.
Figure 8:
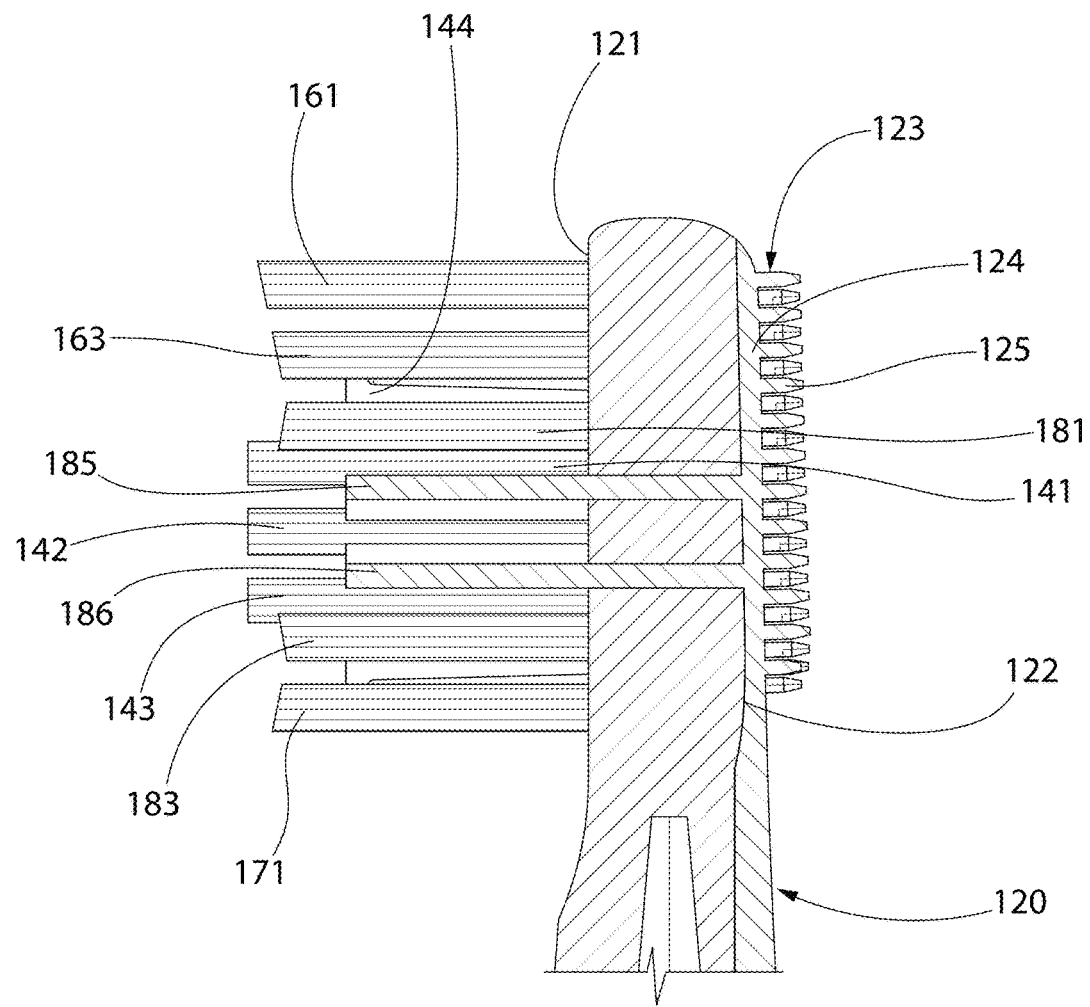
FIG. 8 is a cross-sectional view taken along line VIII-VIII in FIG. 3.

Referring briefly to FIGS. 1, 7, and 8 concurrently, the head 120 comprises a front surface 121 and an opposing rear surface 122. The head 120 may include a soft tissue cleanser 123 positioned on the rear surface 122 of the head 120. In the exemplified embodiment, the soft tissue cleanser 123 comprises a pad portion 124 coupled to the rear surface 122 of the head 120 and protrusions 125 extending from the pad portion 124 in a direction away from the rear surface 122 of the head 120. The soft tissue cleanser 123 may be formed of a resilient material, such as a thermoplastic elastomer, a rubber, silicon, or the like. The soft tissue cleanser 123 may be injection molded directly onto the rear surface 122 of the head 120 during manufacturing in some embodiments. In certain embodiments, one or more elastomeric tooth cleaning elements may be formed integrally with the soft tissue cleanser 123 and extend from the front surface 121 of the head 120 for wiping and/or cleaning a user's teeth. Of course, in certain embodiments the oral care implement 100 may not include any soft tissue cleanser.

Figure 2:
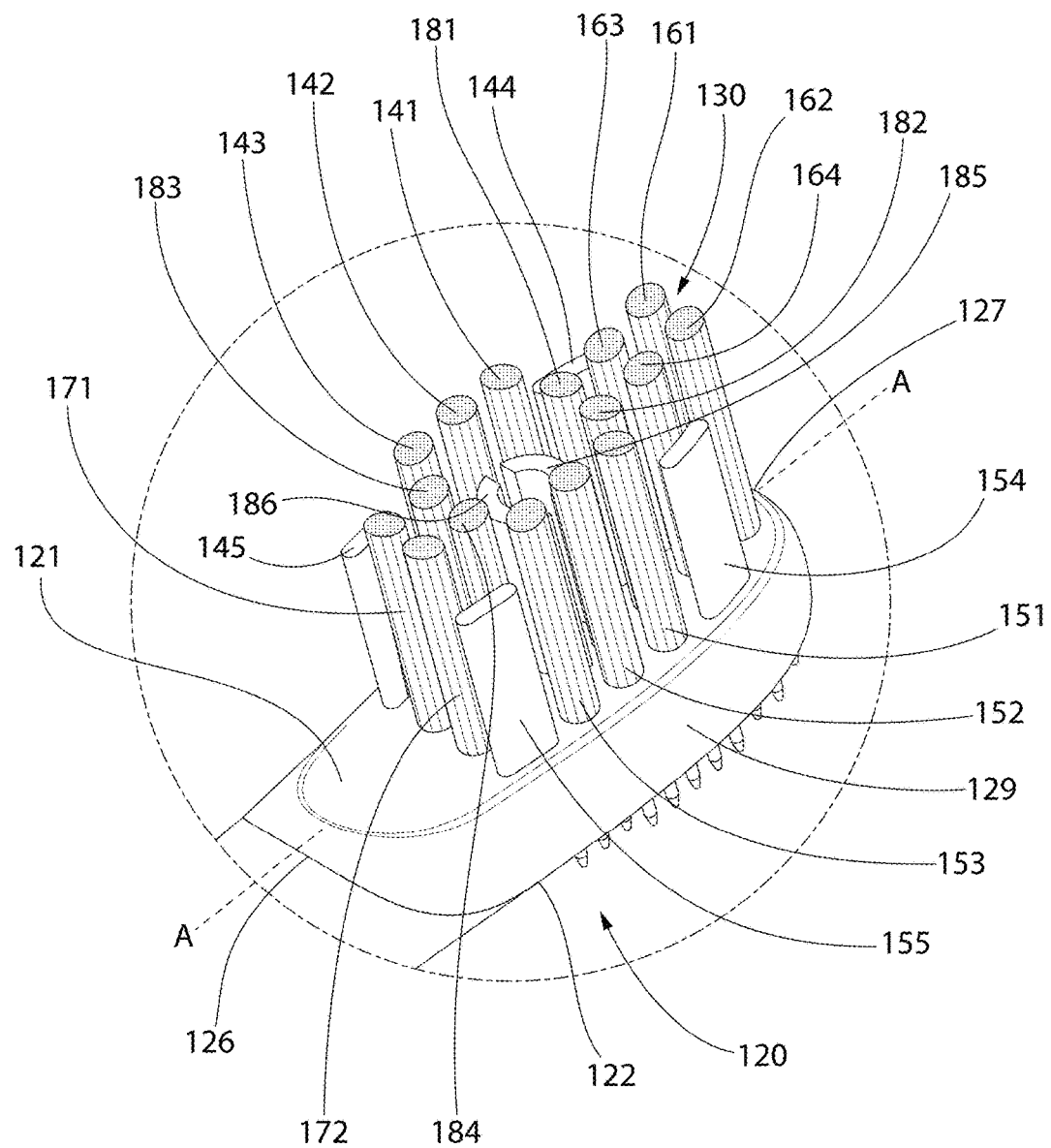
FIG 2 is a close-up view of area II of FIG. 1 illustrating a head of the oral care implement of FIG. 1.
Figure 3:
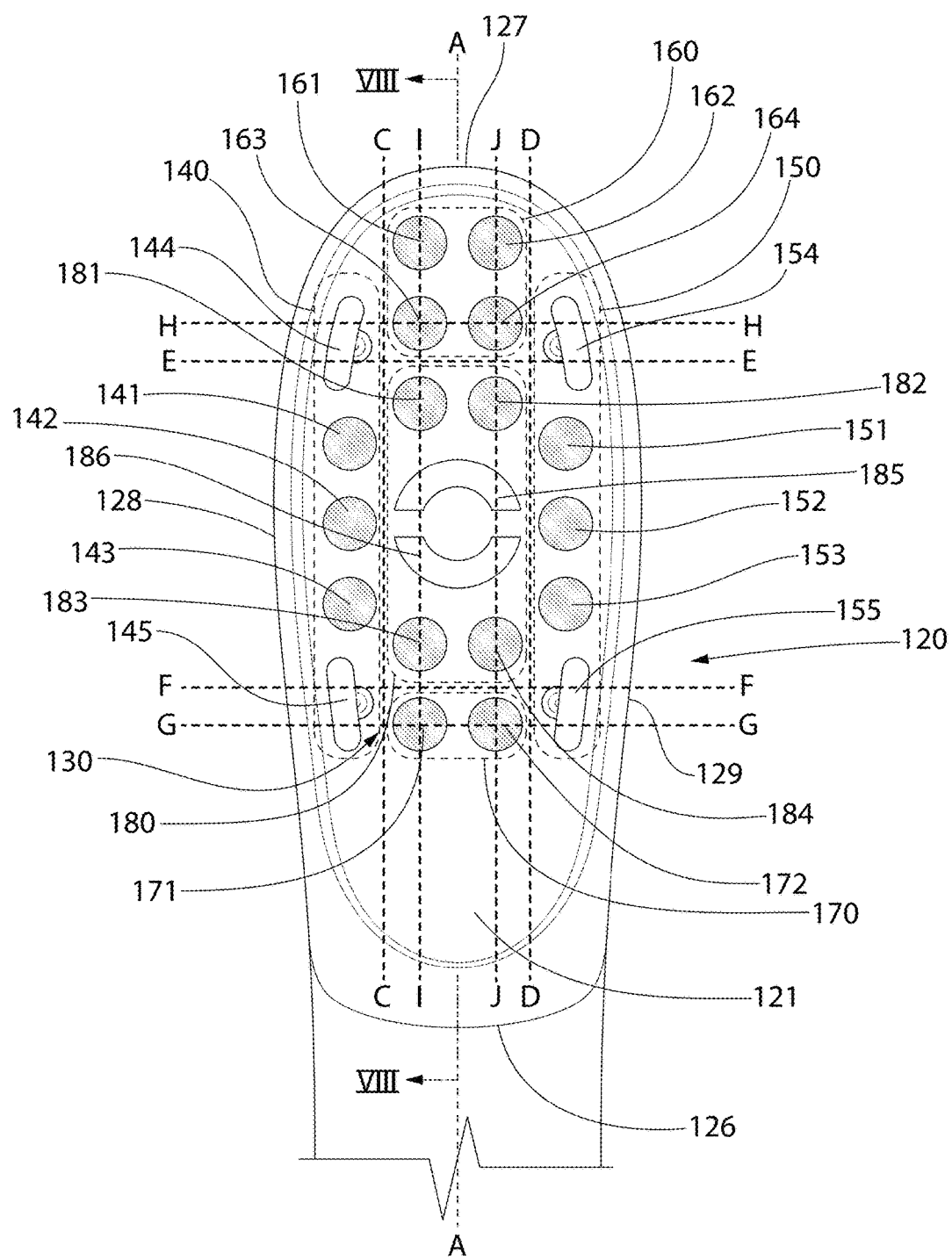
FIG. 3 is a front view of the head of the oral care implement of FIG. 1.

Referring now to FIGS. 1-3 concurrently, the oral care implement 100 will be further described. The head 120 of the oral care implement 100 extends along a longitudinal axis A-A from a proximal end 126 that is adjacent the handle 110 to a distal end 127 that is remote from the handle 110. As noted above, in certain embodiments the soft tissue cleanser 123 may be coupled to or positioned on the rear surface 122 of the head 120. Furthermore, a plurality of tooth cleaning elements 130 extend from the front surface 121 of the head 120. The plurality of tooth cleaning elements 130 are arranged in a tooth cleaning element field and comprise several separate groupings of tooth cleaning elements, which will be described in more detail below.

Although certain details are provided below with regard to the different types of tooth cleaning elements that are coupled to the head 120, in certain embodiments the exact structure, pattern, orientation, and material of the tooth cleaning elements 130 is not to be limiting of the present invention unless so specified in the claims. Thus, unless otherwise described herein, the term "tooth cleaning elements" may refer to any structure that can be used to clean, polish or wipe the teeth and/or soft oral tissue (e.g. tongue, cheek, gums, etc.) through relative surface contact. Common examples of types of tooth cleaning elements may include, without limitation, bristle tufts, filament bristles, fiber bristles, nylon bristles, end-rounded bristles, core-sheath bristles, crimped bristles, spiral bristles, tapered bristles, rubber bristles, elastomeric protrusions, flexible polymer protrusions, combinations thereof and/or structures containing such materials or combinations. Suitable elastomeric materials for elastomeric protrusions may include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 130 can be connected to the head 120 in any manner known in the art. For example, staples/anchors, in-mold tufting (IMT), or anchor free tufting (AFT) could be used to mount the tooth cleaning elements 130 to the head 120. In certain embodiments, the invention can be practiced with various combinations of stapled, IMT, or AFT bristles. In staple technologies, the tooth cleaning elements 130, such as bristles, are bent into a U-shape, clustered together into a tuft of bristles, and then the bight portion of the tuft of bristles is inserted into a tuft hole in the head 120. A staple is then inserted into the tuft hole to engage the bight portion of the tuft of bristles and secure the tuft of bristles to the head 110. In AFT, bristles are inserted through openings in a plate that is a separate structure from the brush head. The free ends of the bristles on one side of the plate or membrane perform the cleaning function. The ends of the bristles on the other side of the plate or membrane are melted together by heat to be anchored in place. After the ends of the bristles are melted together, the plate is secured to the brush head such as by ultrasonic welding.

Where the tooth cleaning elements 130 are elastomeric elements, such elastomeric elements may be formed integrally with the soft tissue cleanser 123 and extend through a passageway formed through the head as illustrated in FIG. 8. Alternatively, the elastomeric elements may be separate from the soft tissue cleanser 123 and anchored to the head 120 using other techniques known in the art.

As will be discussed in more detail below, the tooth cleaning elements 130 may include different types of tooth cleaning elements positioned at different locations on the head. Different types of tooth cleaning elements may impart different benefits to a person using the oral care implement 100. Specifically, and for example only, tapered bristles may offer a gentle brushing and may be preferable for users with sensitive teeth. Tapered bristles may also penetrate into the gaps between the teeth to better clean those interproximal areas. Spiral bristles may be thicker than traditional bristles and may be better for teeth whitening or providing a more thorough clean to a user's teeth. End-rounded bristles are standard bristles that provide a traditional clean or may be preferable for users with tooth and gum sensitivity. Elastomeric elements may wipe and polish the teeth and may also be used for tooth whitening. These different types of tooth cleaning elements may be positioned at different locations on the same head to provide all of the different benefits to a user with a single oral care implement. Depending on the location and positioning of these different types of tooth cleaning elements, the different types of tooth cleaning elements may interact with one another to further enhance the tooth brushing and tooth cleaning experience. There is a desire in the art to find optimal locations for the different types of tooth cleaning elements on a toothbrush or oral care implement head to optimize the benefits of the different types of tooth cleaning elements and increase the efficiency and effectiveness of the tooth cleaning achieved using the toothbrush or oral care implement.

Referring still to FIGS. 1-3, the head 120 of the oral care implement 100 comprises the front surface 121, the rear surface 122, a first peripheral side 128, and a second peripheral side 129 opposite the first peripheral side 128. Each of the first and second peripheral sides 128, 129 extends between the front and rear surfaces 121, 122 of the head 120 and between the proximal end 126 of the head 120 and the distal end 127 of the head 120. Thus, the first and second peripheral sides 128, 129 of the head 120 are the opposing lateral surfaces of the head 120.

As noted above, the plurality of tooth cleaning elements 130 form a tooth cleaning element field and the plurality of tooth cleaning elements 130 are arranged in groupings. Specifically, the tooth cleaning element field comprises a first peripheral grouping of tooth cleaning elements 140 positioned adjacent the first peripheral side 128 of the head 120, a second peripheral grouping of tooth cleaning elements 150 positioned adjacent the second peripheral side 129 of the head 120, a distal grouping of tooth cleaning elements 160 positioned adjacent the distal end 127 of the head 120, and a proximal grouping of tooth cleaning elements 170 positioned adjacent the proximal end 126 of the head 120. The tooth cleaning element field may, in some embodiments, also comprise a central grouping of tooth cleaning elements 180 located laterally between the first and second peripheral groupings of tooth cleaning elements 140, 150 and longitudinally between the distal and proximal groupings of tooth cleaning elements 160, 170. In FIG. 3, each of the groupings of tooth cleaning elements 140, 150, 160, 170, 180 is denoted with a dashed-line encircling that particular grouping to provide clarity regarding which of the tooth cleaning elements are included within each grouping.

Each of the tooth cleaning elements 130 extends from the front surface 121 of the head 120. The various groupings described herein are distinguished based on the positioning of the tooth cleaning elements within that grouping on the front surface 121 of the head 120. Thus, the first peripheral grouping of tooth cleaning elements 140 includes tooth cleaning elements that extend from the front surface 121 of the head 120 at a location that is adjacent to the first peripheral side 128 of the head 120. Similarly, the second peripheral grouping of tooth cleaning elements 150 includes tooth cleaning elements that extend from the front surface 121 of the head 120 at a location that is adjacent to the second peripheral side 129 of the head 120. The distal grouping of tooth cleaning elements 160 includes tooth cleaning elements that extend from the front surface 121 of the head 120 at a location that is adjacent or near the distal end 127 of the head 120. The proximal grouping of tooth cleaning elements 170 includes tooth cleaning elements that extend from the front surface 121 of the head 120 at a location that is adjacent or near the proximal end 126 of the head 120. Finally, the central grouping of tooth cleaning elements 180 includes tooth cleaning elements that extend from the front surface 121 of the head 120 at a central location on the head 120.

The tooth cleaning elements of the first and second peripheral groupings of tooth cleaning elements 140, 150 are located laterally of the other groupings. Specifically, an axis C-C parallel to the longitudinal axis A-A and on a first side of the longitudinal axis A-A that does not pass through any of the cleaning elements separates the first peripheral grouping of tooth cleaning elements 140 from the distal, proximal, and central groupings of tooth cleaning elements 160, 170, 180. An axis D-D parallel to the longitudinal axis A-A on a second side of the longitudinal axis A-A that does not pass through any of the cleaning elements separates the second peripheral grouping of tooth cleaning elements 150 from the distal, proximal, and central groupings of tooth cleaning elements 160, 170, 180. A first axis E-E transverse to the longitudinal axis A-A separates the distal grouping of tooth cleaning elements 160 from the central grouping of tooth cleaning elements 180 and a second axis F-F transverse to the longitudinal axis A-A separates the proximal grouping of tooth cleaning elements 170 from the central grouping of tooth cleaning elements 180. In certain embodiments, the distinction between the proximal, distal, and central tooth cleaning elements 160, 170, 180 may be further recognizable based on the types of cleaning elements within each group or the colors of the cleaning elements of each group. In one embodiment the cleaning elements of the proximal and distal groupings of tooth cleaning elements 160, 170 may have a first color and the cleaning elements of the central grouping of tooth cleaning elements 180 may have a second different color. It should be noted that, as used herein, difference in color only does not amount to a difference in cleaning element "type."

In certain embodiments, with reference to the oral care implement 100 illustrated in FIGS. 1-3, 7, and 8, the first and second peripheral groupings of tooth cleaning elements 140, 150 comprise a first type of tooth cleaning elements and a second type of tooth cleaning elements. Furthermore, the distal and proximal groupings of tooth cleaning elements 160, 170 comprise a third type of tooth cleaning elements. The central grouping of tooth cleaning elements 180 comprises a fourth type of tooth cleaning elements. The central grouping of tooth cleaning elements 180 may also comprise the second type of tooth cleaning elements. In certain embodiments, the first type of tooth cleaning elements may be a tapered bristle, the second type of tooth cleaning elements may be an elastomeric element, such as a lamella or other tooth cleaning feature formed of a thermoplastic elastomer, rubber, or other resilient material, the third type of tooth cleaning element may be a spiral bristle, and the fourth type of tooth cleaning element may be a single component end-rounded bristle. In some embodiments the first and second peripheral groupings of tooth cleaning elements 140, 150 may consist of the first and second types of tooth cleaning elements, which may be the tapered bristles and the elastomeric elements. In some embodiments the distal and proximal groupings of tooth cleaning elements 160, 170 may consist of the third types of tooth cleaning elements, which may be spiral bristles. In some embodiments the central grouping of tooth cleaning elements 180 may consist of the second and fourth types of tooth cleaning elements, which may be the elastomeric elements and the single component end-rounded bristles.

Thus, in certain embodiments each of the first, second, third, and fourth types of tooth cleaning elements are different types of tooth cleaning elements. In certain embodiments, regardless of the specific type of tooth cleaning element associated with each grouping of tooth cleaning elements 140, 150, 160, 170, 180, the first, second, third, and fourth types of tooth cleaning elements may be selected from tapered bristles, elastomeric elements, spiral bristles, single component end-rounded bristles, core-sheath bristles, and crimped bristles. Thus, in one embodiment the type of tooth cleaning element is differentiated based on the structure or shape or material make-up of the tooth cleaning element. In other embodiments, the type of tooth cleaning element may be differentiated based on an oral care additive that is associated with, embedded within, or that forms a part of the tooth cleaning element. Such oral care additives may include, without limitation, lotus seed; lotus flower, bamboo salt; jasmine; corn mint; camellia; aloe; gingko; tea tree oil; xylitol; sea salt; vitamin C; ginger; cactus; baking soda; pine tree salt; green tea; white pearl; black pearl; charcoal powder; nephrite or jade and Ag/Au+. Thus, the first type of tooth cleaning element may be a tooth cleaning element comprising charcoal powder and the second type of tooth cleaning element may be a tooth cleaning element comprising black pearl, etc. Oral care additives in addition to those specifically recited herein and that are known in the art, such as anti-sensitivity agents, anti-bacterial agents, tooth whitening agents, or the like may also be used to differentiate the tooth cleaning elements by type.

The first peripheral grouping of tooth cleaning elements 140 is a grouping of tooth cleaning elements that is positioned nearest to the first peripheral side 128 of the head 120. The first peripheral grouping of tooth cleaning elements 140 comprises the first type of tooth cleaning element and the second type of tooth cleaning element. More specifically, the first peripheral grouping of tooth cleaning elements 140 comprises a first bristle tuft 141, a second bristle tuft 142, a third bristle tuft 143, a first elastomeric element 144, and a second elastomeric element 145. In the exemplified embodiment, the first, second, and third bristle tufts 141, 142, 143 of the first peripheral grouping of tooth cleaning elements 140 comprise a first type of tooth cleaning elements (i.e., tapered bristles). Furthermore, in the exemplified embodiment the second type of tooth cleaning element of the first peripheral grouping of tooth cleaning elements 140 is the first and second elastomeric elements 144, 145.

Although described herein as the first peripheral grouping of tooth cleaning elements 140 having three bristle tufts 141-143, the invention is not to be limited in all embodiments. The first peripheral grouping of tooth cleaning elements 140 may include more or less than three bristle tufts in other embodiments. Similarly, although described herein as the first peripheral grouping of tooth cleaning elements 140 having two elastomeric elements 144, 145, the invention is not to be so limited in all embodiments and the first peripheral grouping of tooth cleaning elements 140 may include more or less than two elastomeric elements.

Figure 4A:
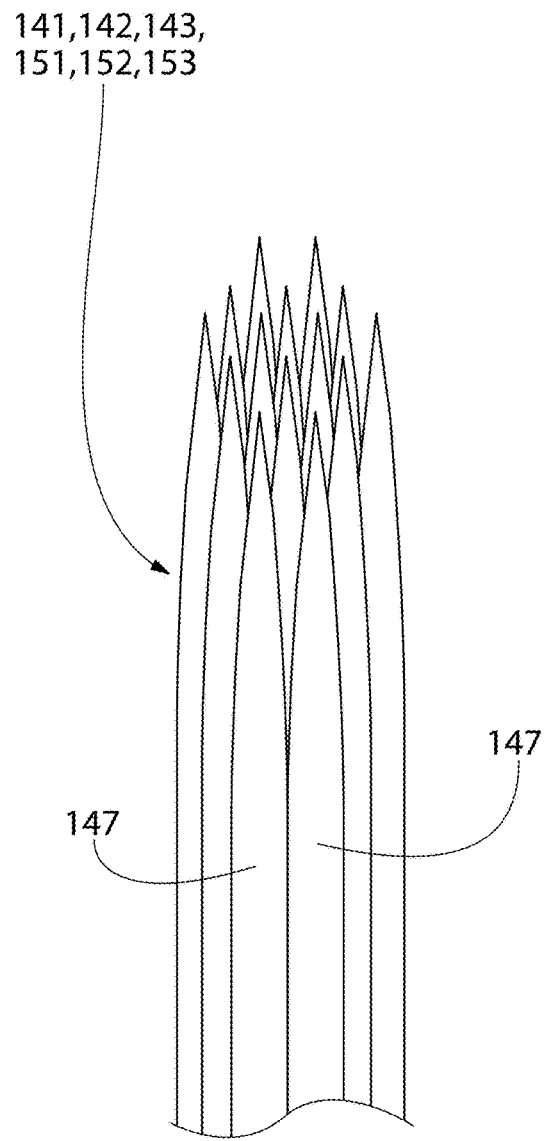
FIG. 4A is a bristle tuft having tapered bristles in accordance with an embodiment of the present invention.
Figure 4B:
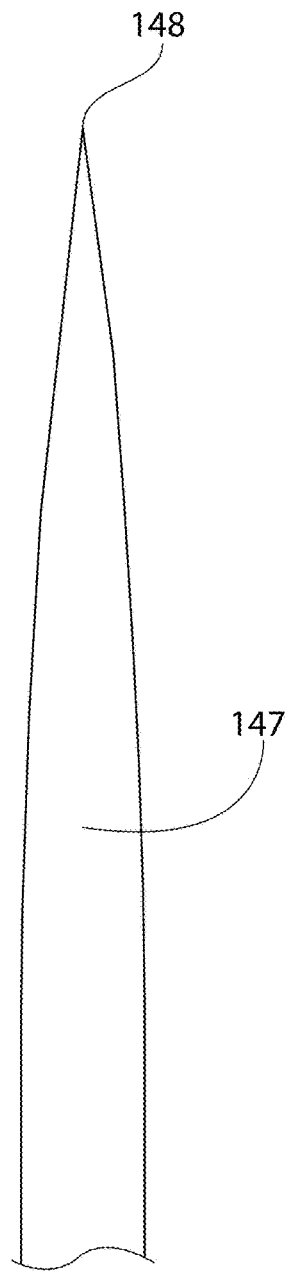
FIG. 4B is a single tapered bristle of the bristle tuft of FIG. 4A.

In the exemplified embodiment, the first type of tooth cleaning elements is tapered bristles. FIG. 4A illustrates the first, second, and third bristle tufts 141, 142, 143. In this embodiment, each of the first, second, and third bristle tufts 141, 142, 143 comprises a plurality of tapered bristles 147. FIG. 4B illustrates a single one of the tapered bristles 147. In the exemplified embodiment, each of the first, second, and third bristle tufts 141, 142, 143 consists of tapered bristles 147 such that only tapered bristles 147 are included in the first, second, and third bristle tufts 141, 142, 143. As illustrated in FIG. 4B, the tapered bristles 147 taper from the end of the bristle that is coupled to the head 120 towards a tip 148 of the tapered bristle 147 along at least a portion of its length. Thus, the cross-sectional area of the tapered bristle 147 decreases either along its entire length in a direction of the tip 148 of the tapered bristle 147 or along a portion of its length in the direction of the tip 148 of the tapered bristle. In certain embodiments, a distal end portion of the tapered bristle 147 that includes the tip 148 may have a different color than the remainder of the tapered bristle 147 to highlight the tapered tip 148, although this is not required in all embodiments.

Referring back to FIGS. 2 and 3, in the exemplified embodiment, the first, second, and third bristle tufts 141, 142, 143 of the first peripheral grouping of tooth cleaning elements 140 comprises the first type of tooth cleaning elements, which is a tapered bristle such as the tapered bristle 147 illustrated in FIGS. 4A and 4B. Furthermore, the first peripheral grouping of tooth cleaning elements 140 comprises the second type of tooth cleaning elements which are the elastomeric elements 144, 145. Thus, the first peripheral grouping of tooth cleaning elements 140 comprises (or in some embodiments consists of) the first and second types of tooth cleaning elements, the first type of tooth cleaning element being tapered bristles and the second type of tooth cleaning element being elastomeric elements.

In the exemplified embodiment, within the first peripheral grouping of tooth cleaning elements 140, the first type of tooth cleaning element are positioned between the second type of tooth cleaning elements. More specifically, the first, second, and third bristle tufts 141, 142, 143 comprising the tapered bristles 147 are positioned longitudinally between the first and second elastomeric elements 144, 145. Thus, the first and second elastomeric elements 144, 145 anchor the top and bottom of the first peripheral grouping of tooth cleaning elements 140 and the first, second, and third bristle tufts 141, 142, 143 are positioned therebetween. Furthermore, in the exemplified embodiment the first type of tooth cleaning elements (i.e., the tapered bristles 147) extend from the front surface 121 of the head 120 a distance that is greater than the distance that the second type of tooth cleaning elements (i.e., the elastomeric elements 144, 145) extend from the front surface 121 of the head 120, as best illustrated in FIGS. 2, 7, and 8.

The second peripheral grouping of tooth cleaning elements 150 is a grouping of tooth cleaning elements that is positioned nearest to the second peripheral side 129 of the head 120. The second peripheral grouping of tooth cleaning elements 150 comprises the first type of tooth cleaning element and the second type of tooth cleaning element. More specifically, the second peripheral grouping of tooth cleaning elements 150 comprises a first bristle tuft 151, a second bristle tuft 152, a third bristle tuft 153, a first elastomeric element 154, and a second elastomeric element 155. In the exemplified embodiment, the first, second, and third bristle tufts 151, 152, 153 of the second peripheral grouping of tooth cleaning elements 150 comprise the first type of tooth cleaning elements (i.e., tapered bristles. Furthermore, in the exemplified embodiment the second type of tooth cleaning element of the second peripheral grouping of tooth cleaning elements 150 is the first and second elastomeric elements 154, 155.

Although described herein as the second peripheral grouping of tooth cleaning elements 150 having three bristle tufts 151-153, the invention is not to be limited in all embodiments. The second peripheral grouping of tooth cleaning elements 150 may include more or less than three bristle tufts in other embodiments. Similarly, although described herein as the second peripheral grouping of tooth cleaning elements 150 having two elastomeric elements 154, 155, the invention is not to be so limited in all embodiments and the second peripheral grouping of tooth cleaning elements 150 may include more or less than two elastomeric elements.

In the exemplified embodiment, the first type of tooth cleaning elements are tapered bristles such as those illustrated in FIGS. 4A and 4B and described above. In the exemplified embodiment, the first, second, and third bristle tufts 151, 152, 153 of the second peripheral grouping of tooth cleaning elements 150 comprises the first type of tooth cleaning elements, which is a tapered bristle such as the tapered bristle 147 illustrated in FIGS. 4A and 4B. Furthermore, the second peripheral grouping of tooth cleaning elements 150 comprises the second type of tooth cleaning elements which are the elastomeric elements 154, 155. Thus, the second peripheral grouping of tooth cleaning elements 150 comprises (or in some embodiments consists of) the first and second types of tooth cleaning elements, the first type of tooth cleaning element being tapered bristles and the second type of tooth cleaning element being elastomeric elements.

In the exemplified embodiment, within the second peripheral grouping of tooth cleaning elements 150, the first type of tooth cleaning element is positioned between the second type of tooth cleaning element. More specifically, the first, second, and third bristle tufts 151, 152, 153 comprising the tapered bristles 147 (or the first type of tooth cleaning element) are positioned longitudinally between the first and second elastomeric elements 154, 155. Thus, the first and second elastomeric elements 154, 155 anchor the top and bottom of the second peripheral grouping of tooth cleaning elements 150 and the first, second, and third bristle tufts 151, 152, 153 are positioned therebetween. Furthermore, the first type of tooth cleaning elements (i.e., the first, second, and third bristle tufts 151, 152, 153 comprising or consisting of the tapered bristles 147) extend from the front surface 121 of the head 120 a distance that is greater than the distance that the second type of tooth cleaning elements (i.e., the elastomeric elements 154, 155) extend from the front surface 121 of the head 120, as best illustrated in FIGS. 2, 7, and 8.

In the exemplified embodiment, the first peripheral grouping of tooth cleaning elements 140 are transversely aligned with the second peripheral grouping of tooth cleaning elements 150 and are symmetrical about the longitudinal axis A-A. Specifically, the first and second elastomeric elements 144, 145 of the first peripheral grouping of tooth cleaning elements 140 are transversely aligned with the respective first and second elastomeric elements 154, 155 of the second peripheral grouping of tooth cleaning elements 150, and the first, second, and third bristle tufts 141, 142, 143 of the first peripheral grouping of tooth cleaning elements 140 are transversely aligned with the respective first, second, and third bristle tufts 151, 152, 153 of the second peripheral grouping of tooth cleaning elements 150. In one embodiment the first and second peripheral groupings of tooth cleaning elements 140, 150 are identical but located on the opposing sides of the front surface 121 of the head 120.

In the exemplified embodiment, the distal grouping of tooth cleaning elements 160 is the grouping of tooth cleaning elements that is positioned nearest to the distal end 127 of the head 120. The distal grouping of tooth cleaning elements 160 comprises the third type of tooth cleaning element. More specifically, the distal grouping of tooth cleaning elements 160 comprises a first, second, third, and fourth bristle tuft 161, 162, 163, 164 that are positioned adjacent to the distal end 127 of the head 120. In the exemplified embodiment, the first, second, third, and fourth bristle tufts 161, 162, 163, 164 are positioned in a square or rectangular-like arrangement in two rows and two columns, although other arrangements are possible and within the scope of this application. Furthermore, although four bristle tufts 161-164 are exemplified within the distal grouping of tooth cleaning elements 160, the invention is not to be limited by this in all embodiments and the distal grouping of tooth cleaning elements 160 may include more or less than four bristle tufts in other embodiments (such as one bristle tuft, two bristle tufts, three bristle tufts, five bristle tufts, six bristle tufts, or the like).

Figures 5A, 5B:
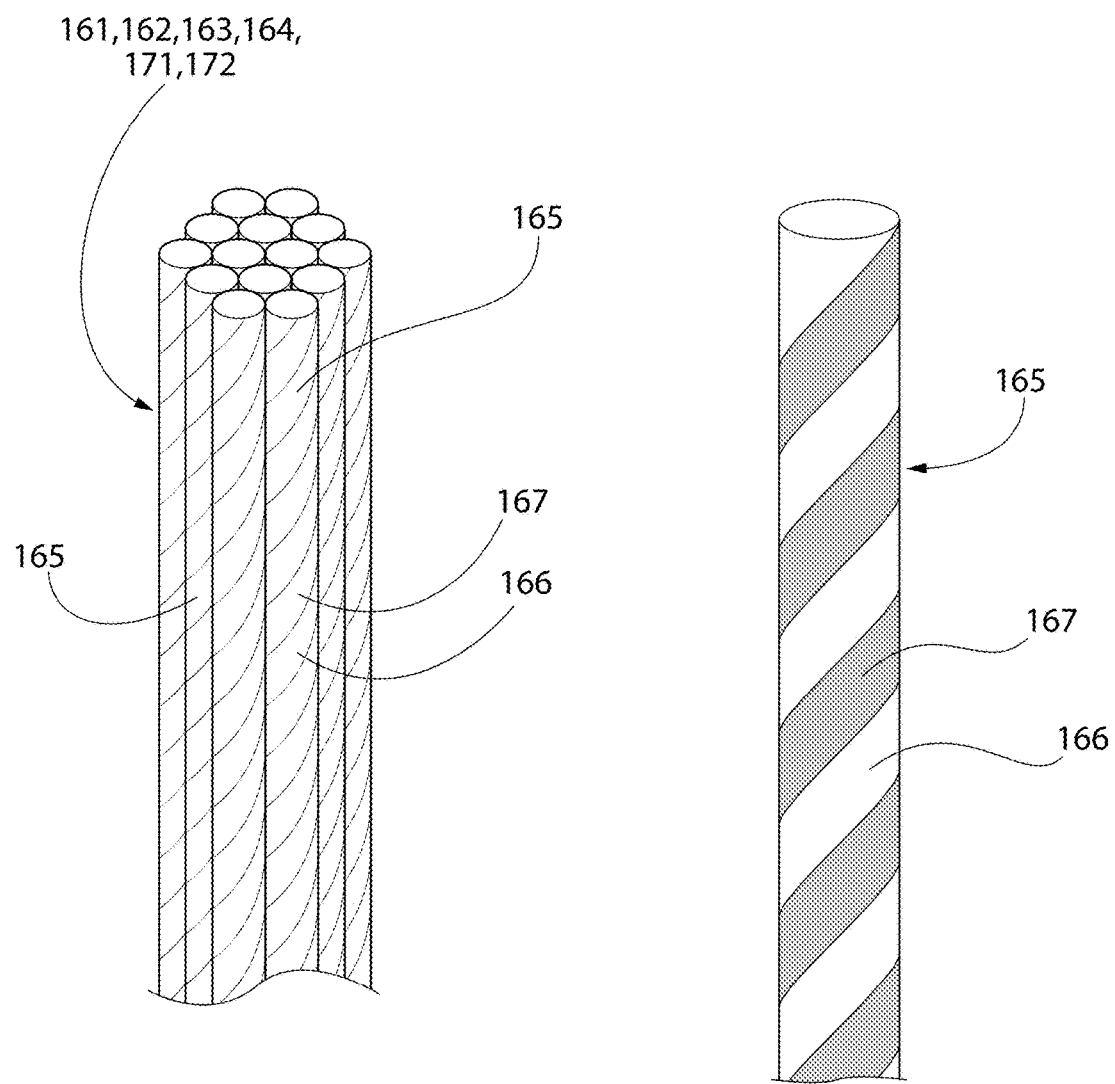
FIG. 5A is a bristle tuft having spiral bristles in accordance with an embodiment of the present invention.
FIG. 5B is a single spiral bristle of the bristle tuft of FIG. 5A.

The distal grouping of tooth cleaning elements 160 comprises a third type of tooth cleaning elements. In some embodiments the distal grouping of tooth cleaning elements 160 may consist of the third type of tooth cleaning elements. In certain embodiments the third type of tooth cleaning elements comprises, or in some embodiments consists of, spiral bristles. Thus, the first, second, third, and fourth bristle tufts 161, 162, 163, 164 are tufts of spiral bristles. FIG. 5A illustrates the first, second, third, and fourth bristle tufts 161, 162, 163, 164 comprising spiral bristles 165. FIG. 5B illustrates one of the spiral bristles 165. The spiral bristle 165 may be formed from two monofilaments or strand components 166, 167 that are wound or intertwined together. The two monofilaments 166, 167 may be the same color as illustrated in FIG. 5A or a different color as illustrated in FIG. 5B. The spiral bristle 165 may be end-rounded, tapered, or the like as desired.

In certain embodiments, each of the first, second, third, and fourth bristle tufts 161, 162, 163, 164 of the distal grouping of tooth cleaning elements 160 comprises spiral bristles 165. In other embodiments each of the first, second, third, and fourth bristle tufts 161, 162, 163, 164 of the distal grouping of tooth cleaning elements 160 consists of spiral bristles 165. Thus, the distal grouping of tooth cleaning elements 160 may in some embodiments comprise and in other embodiments consist of the third type of tooth cleaning elements, which in this embodiment is spiral bristles 165.

In the exemplified embodiment (as best illustrated in FIGS. 2, 7 and 8), the height that the distal grouping of tooth cleaning elements 160 extends from the front surface 121 of the head 120 increases in the direction of the distal end 127 of the head 120. More specifically, there is a gradual and continuous increase in height from a proximal-most point 168 of the distal grouping of tooth cleaning elements 160 to the distal-most point 169 of the distal grouping of tooth cleaning elements 160. In that regard, each of the first, second, third, and fourth bristle tufts 161, 162, 163, 164 of the distal grouping of tooth cleaning elements 160 terminates in a free end that is slanted or angled relative to the front surface 121 of the head 120 such that the taller part at the free end is nearer to the distal end of the head 127.

As noted above, the proximal grouping of tooth cleaning elements 170 is the grouping of tooth cleaning elements positioned nearest to the proximal end 126 of the head 120 adjacent to the handle 110. In the exemplified embodiment the proximal grouping of tooth cleaning elements 170 comprises a first and second bristle tuft 171, 172 that are positioned adjacent to the proximal end 126 of the head 120. In the exemplified embodiment, the first and second bristle tufts 171, 172 are positioned in transverse alignment on opposing sides of the longitudinal axis A-A of the head 120, but the invention is not to be limited by this positioning in all embodiments. Although two bristle tufts 171, 172 are exemplified within the proximal grouping of tooth cleaning elements 170, the invention is not to be so limited in all embodiments. Rather, the proximal grouping of tooth cleaning elements 170 may include a single bristle tuft or more than two bristle tufts in other embodiments.

In the exemplified embodiment, the proximal grouping of tooth cleaning elements 170 comprises (or in some embodiments consists of) the third type of tooth cleaning elements, which as described above is the spiral bristles 165 in the exemplified embodiment. Thus, in the exemplified embodiment each of the first and second bristle tufts 171, 172 of the proximal grouping of tooth cleaning elements 170 comprises, or in some embodiments consists of, the spiral bristles 165. Thus, each of the first and second bristle tufts 171, 172 is a bristle tuft containing the spiral bristles 165, as depicted in FIGS. 5A and 5B. Furthermore, as illustrated in FIGS. 2, 7, and 8, in the exemplified embodiment the first and second bristle tufts 171, 172, individually and collectively, extend a height from the front surface 121 of the head 120 that gradually and continually decreases with longitudinal distance from the proximal end 126 of the head 120 towards the distal end 127 of the head 120.

The central grouping of tooth cleaning elements 180 is located centrally on the head 120 and is bounded by the proximal grouping of tooth cleaning elements 170 to the bottom, the distal grouping of tooth cleaning elements 160 to the top, the first peripheral grouping of tooth cleaning elements 140 to the left, and the second peripheral grouping of tooth cleaning elements 150 to the right. In one embodiment, the central grouping of tooth cleaning elements 180 comprises the second type of tooth cleaning element and a fourth type of tooth cleaning element. As discussed above, the second type of tooth cleaning element may be elastomeric elements. The fourth type of tooth cleaning element may be single component end-rounded bristles.

Figures 6A, 6B:
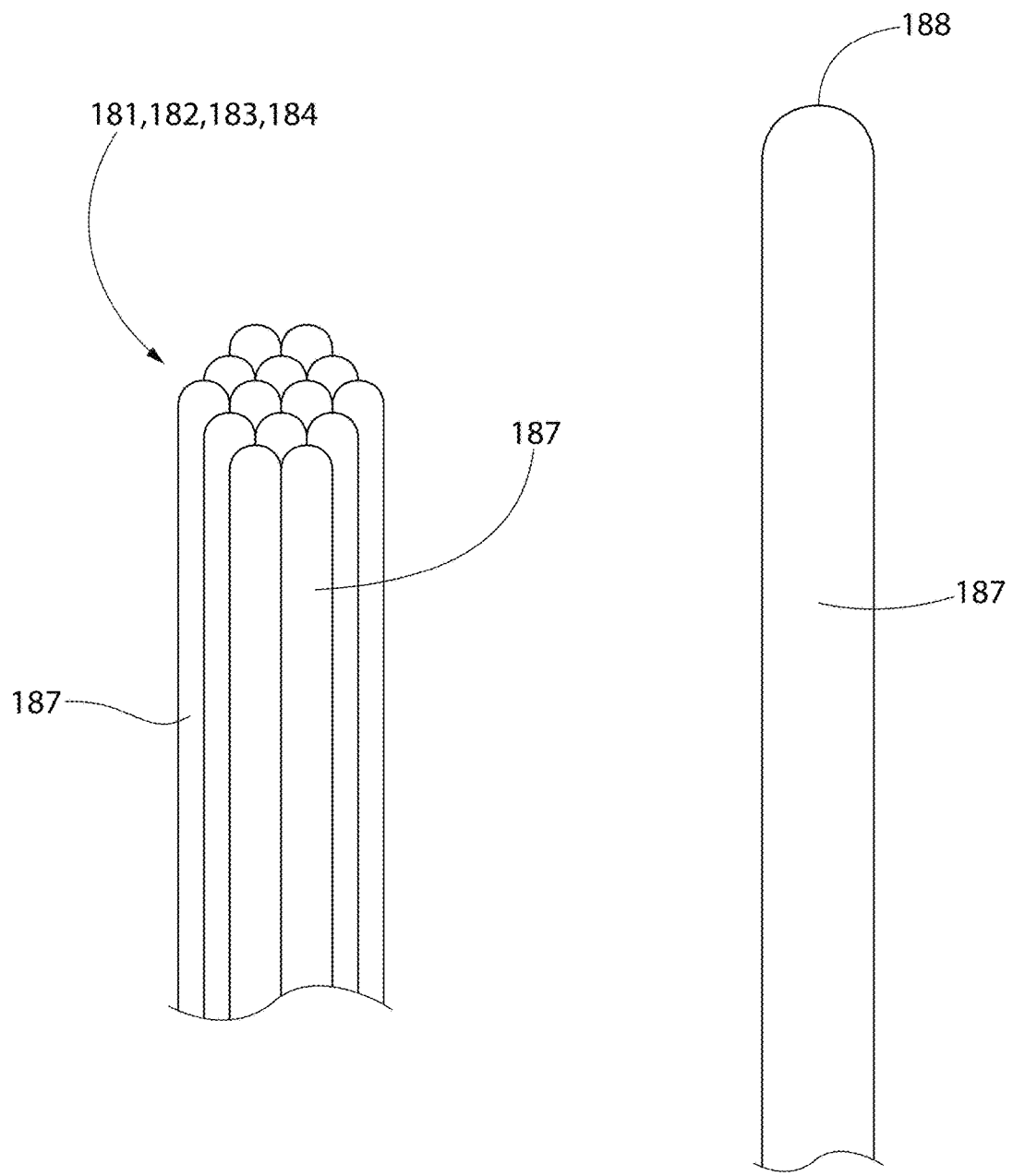
FIG. 6A is a bristle tuft having end-rounded bristles in accordance with an embodiment of the present invention.
FIG. 6B is a single end-rounded bristle of the bristle tuft of FIG. 6A.

In that regard, the central grouping of tooth cleaning elements 180 comprises a first bristle tuft 181, a second bristle tuft 182, a third bristle tuft 183, a fourth bristle tuft 184, a first elastomeric element 185, and a second elastomeric element 186. In certain embodiments, each of the first, second, third, and fourth bristle tufts 181-184 may comprise the fourth type of tooth cleaning element, which may be a single component end-rounded bristle. FIG. 6A illustrates the first, second, third, and fourth bristle tufts 181-184 of the central grouping of tooth cleaning elements 180 comprising single component end-rounded bristles 187 and FIG. 6B illustrates one of the single component end-rounded bristles 187. The end-rounded bristle 187 is a monofilament or single component having an rounded tip or distal end 188. The single component end-rounded bristle 187 may be white or colored or combinations of the two within a single one of the bristles 187 or among the various bristles in each bristle tuft 181-184 or in the different bristle tufts 181-184.

Returning to FIGS. 2 and 3, in the exemplified embodiment, within the central grouping of tooth cleaning elements 180, the second type of tooth cleaning elements (i.e., the elastomeric elements 185, 186) are located longitudinally between the fourth types of tooth cleaning elements (i.e., the bristle tufts 181-184 comprising the single component end-rounded bristles 187). The elastomeric elements 185, 186 are each arcuate shaped elements having concave surfaces that face one another and the centerpoint of the head 120. The elastomeric elements 185, 186 are positioned adjacent one another so as to form a loop. The first and second bristle tufts 181, 182 are positioned adjacent to a convex surface of the first elastomeric element 185 and the third and fourth bristle tufts 183, 184 are positioned adjacent to a convex surface of the second elastomeric element 186. In the exemplified embodiment, the first, second, and third tufts of bristles 141, 142, 143, 151, 152, 153 of the first and second peripheral groupings of tooth cleaning elements 140, 150 and the tufts of bristles 181, 182, 183, 184 of the central grouping of tooth cleaning elements 180 collectively form a loop that surrounds the first and second elastomeric elements 185, 186 of the central grouping of tooth cleaning elements 180.

Furthermore, there exists a transverse axis or plane G-G that is perpendicular to the longitudinal axis A-A that intersects the second elastomeric elements 145, 155 of the first and second peripheral groupings of tooth cleaning elements 140, 150 and the first and second bristle tufts 171, 172 of the proximal grouping of tooth cleaning elements 170. Similarly, there exists a transverse axis or plane H-H that is perpendicular to the longitudinal axis A-A that intersects the first elastomeric elements 144, 154 of the first and second peripheral groupings of tooth cleaning elements 140, 150 and the third and fourth bristle tufts 163, 164 of the distal grouping of tooth cleaning elements 160.

The first and third bristle tufts 161, 163 of the distal grouping of tooth cleaning elements 160, the first and third bristle tufts 181, 183 of the central grouping of tooth cleaning elements 180, and the first bristle tuft 171 of the proximal grouping of tooth cleaning elements 170 are aligned along an axis I-I that is parallel to the longitudinal axis A-A of the head 120. Similarly, the second and fourth bristle tufts 162, 164 of the distal grouping of tooth cleaning elements, the second and fourth bristle tufts 182, 184 of the central grouping of tooth cleaning elements 180, and the second bristle tuft 172 of the proximal grouping of tooth cleaning elements 170 are aligned along an axis J-J that is parallel to the longitudinal axis A-A of the head 120.

Referring to FIGS. 7 and 8, a comparison of the heights of the different tooth cleaning elements will be discussed. As noted above, the first, second, and third bristle tufts 141-143, 151-153 of the first and second peripheral groupings of tooth cleaning elements 140, 150 are taller (measured from the front surface 121 of the head 120 to the terminal ends of the cleaning elements) than the elastomeric elements 144, 145, 154, 155 in the first and second peripheral groupings of tooth cleaning elements 140, 150. The first, second, and third bristle tufts 141-143, 151-153 of the first and second peripheral groupings of tooth cleaning elements 140, 150 may also be taller than the bristle tufts 181-184 and the elastomeric elements 185, 186 of the central grouping of tooth cleaning elements 180. In certain embodiments, as illustrated in FIG. 8, the bristle tufts 171 of the proximal grouping of tooth cleaning elements 170 and the bristle tufts 161 of the distal grouping of tooth cleaning elements 160 have a maximum height that is greater than a maximum height of the bristle tufts 181, 183 and the elastomeric elements 185, 186 of the central grouping of tooth cleaning elements 180 thereby creating a concave profile along the longitudinal axis A-A.

Figure 9:
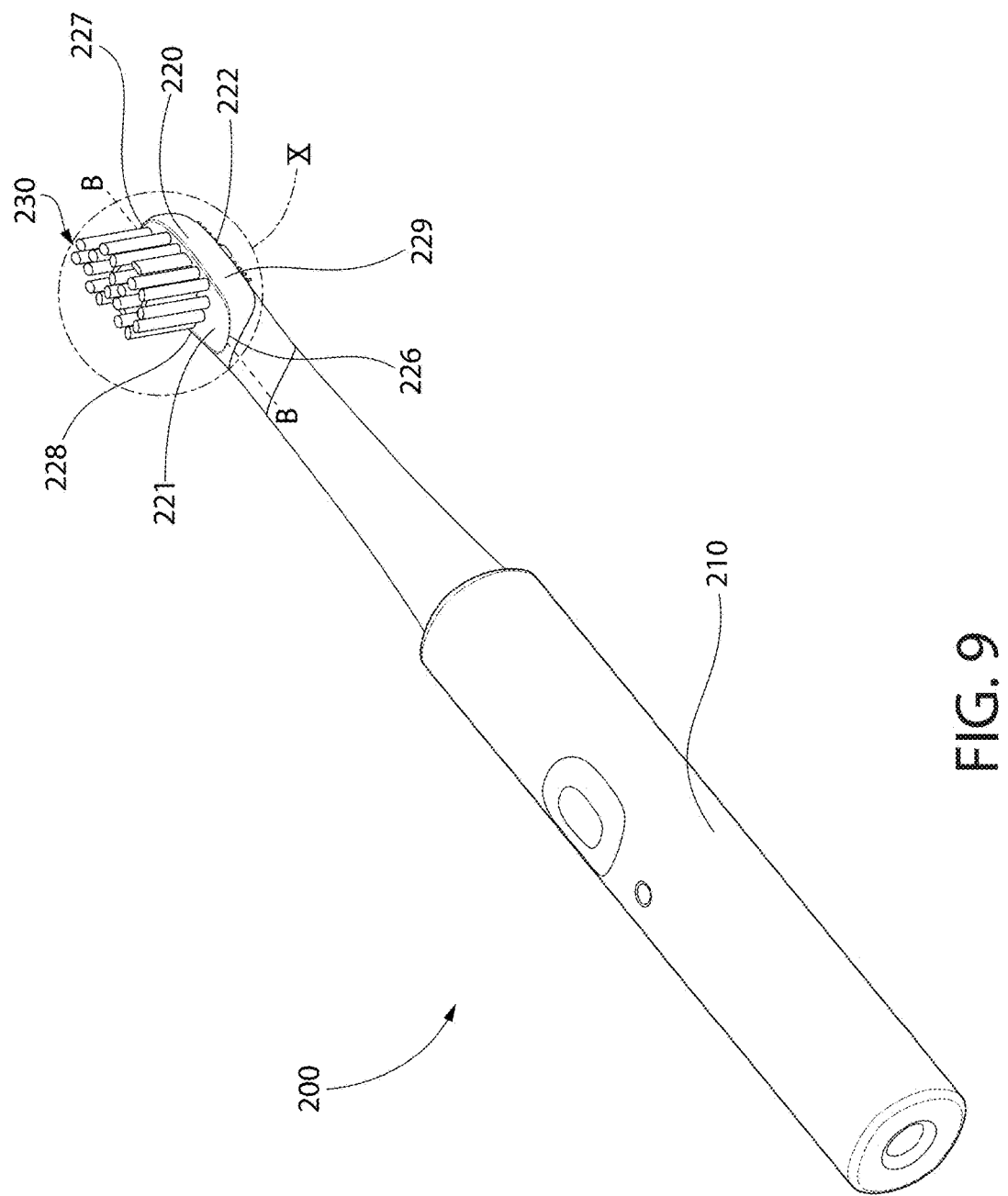
FIG. 9 is a front perspective view of an oral care implement in accordance with a second embodiment of the present invention.
Figure 10:
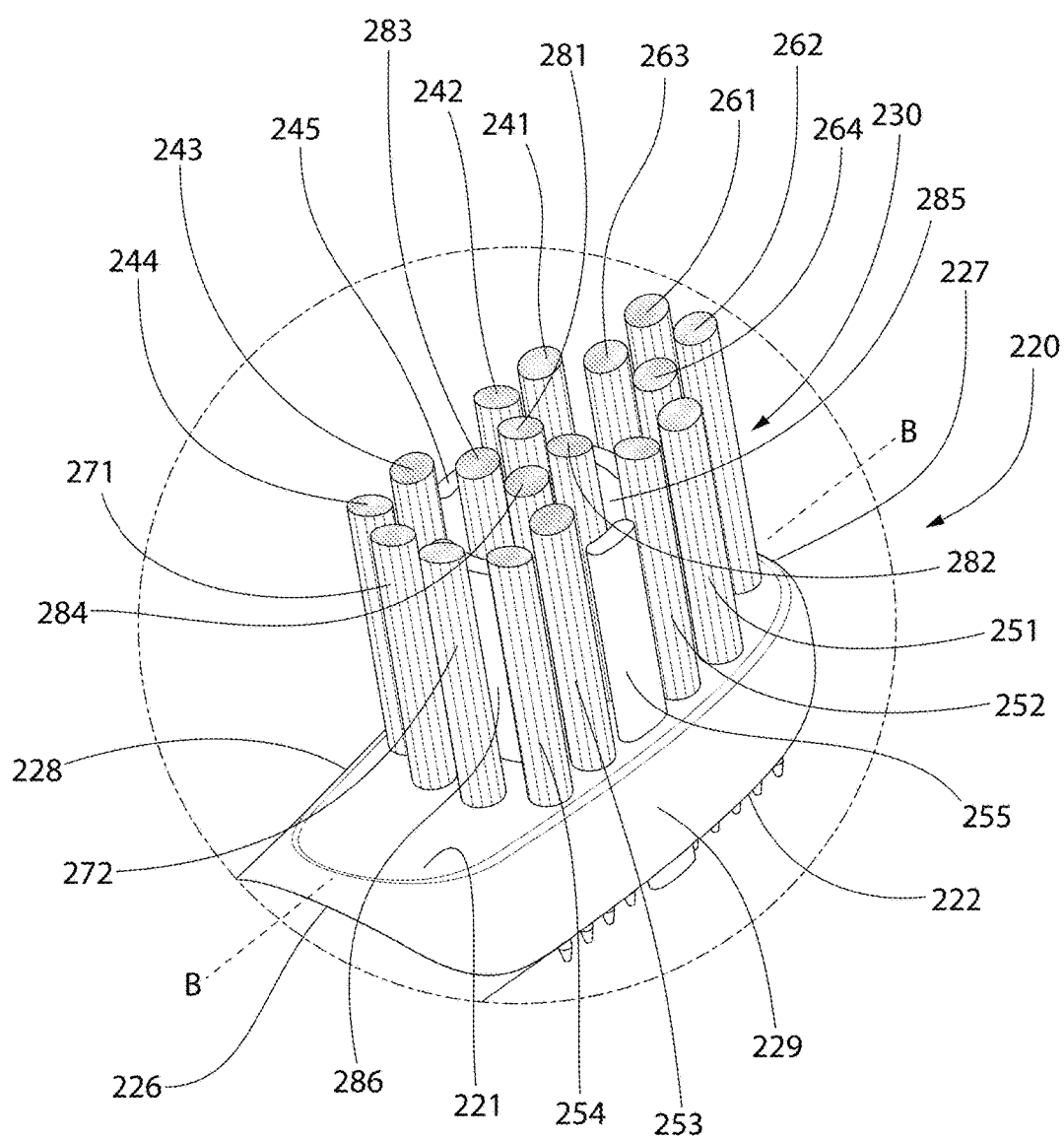
FIG. 10 is a close-up view of area X of FIG. 9 illustrating a head of the oral care implement of FIG. 9.
Figure 11:
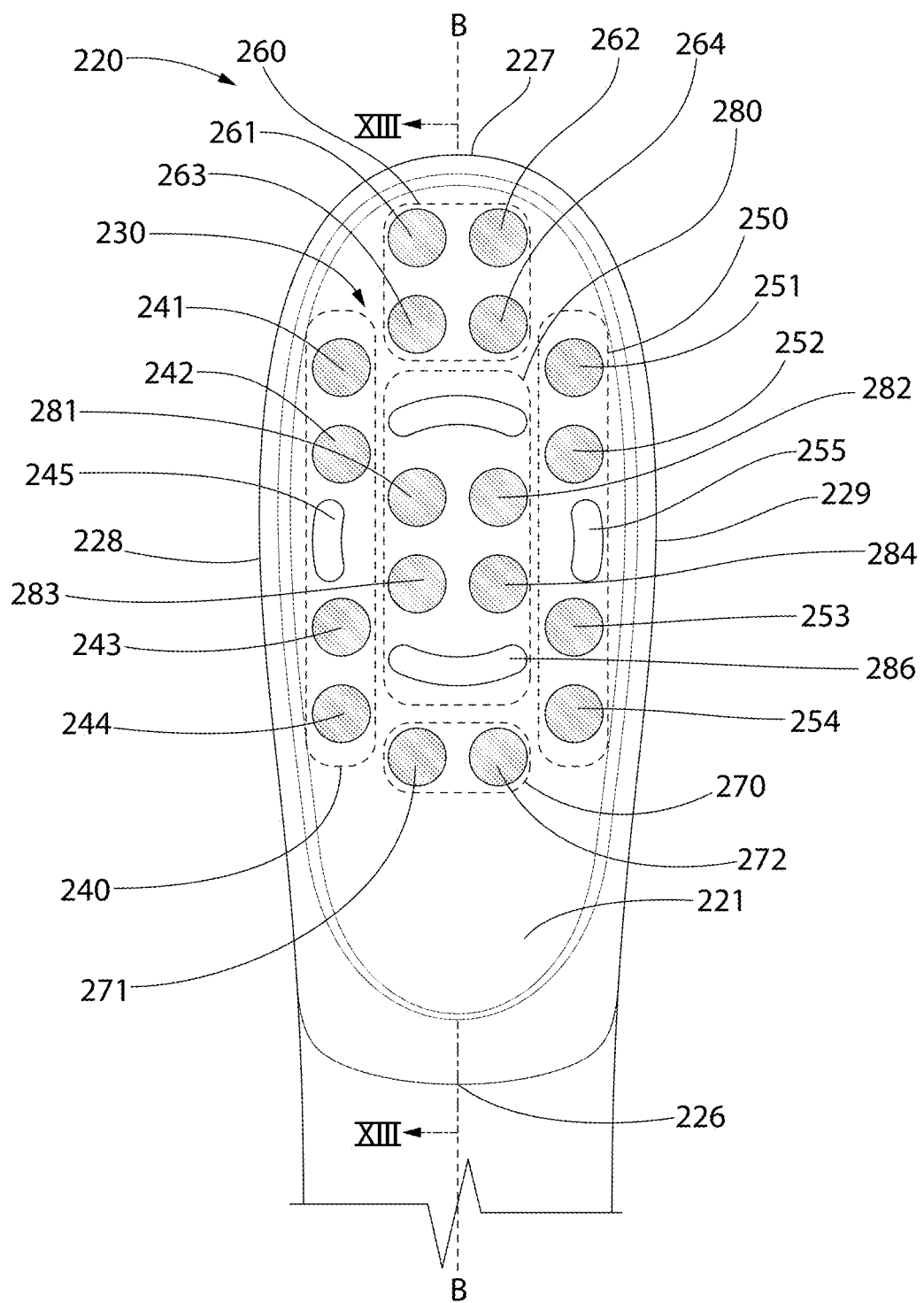
FIG. 11 is a front view of the head of the oral care implement of FIG. 9.
Figure 12:
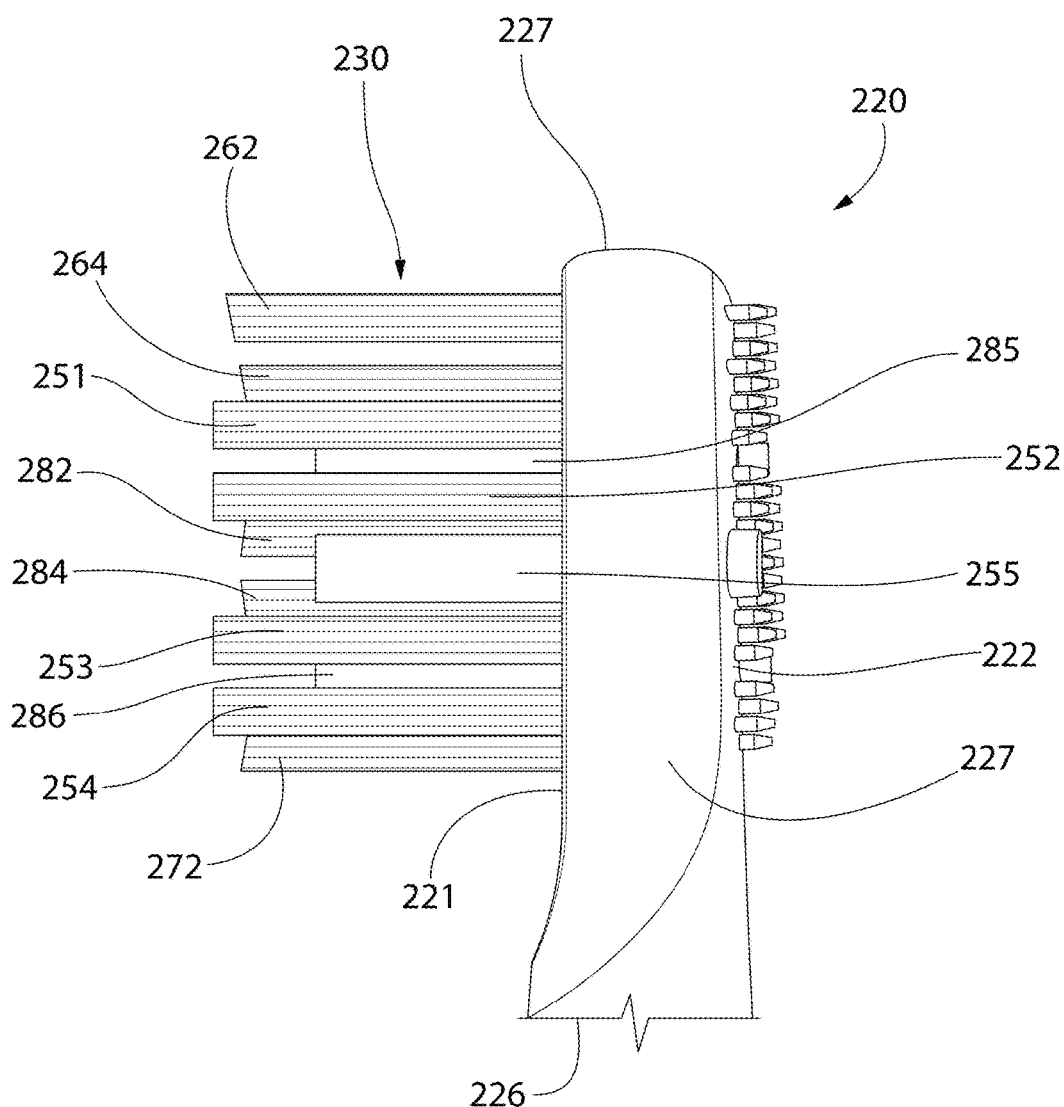
FIG. 12 is a side view of the head of the oral care implement of FIG. 9.
Figure 13:
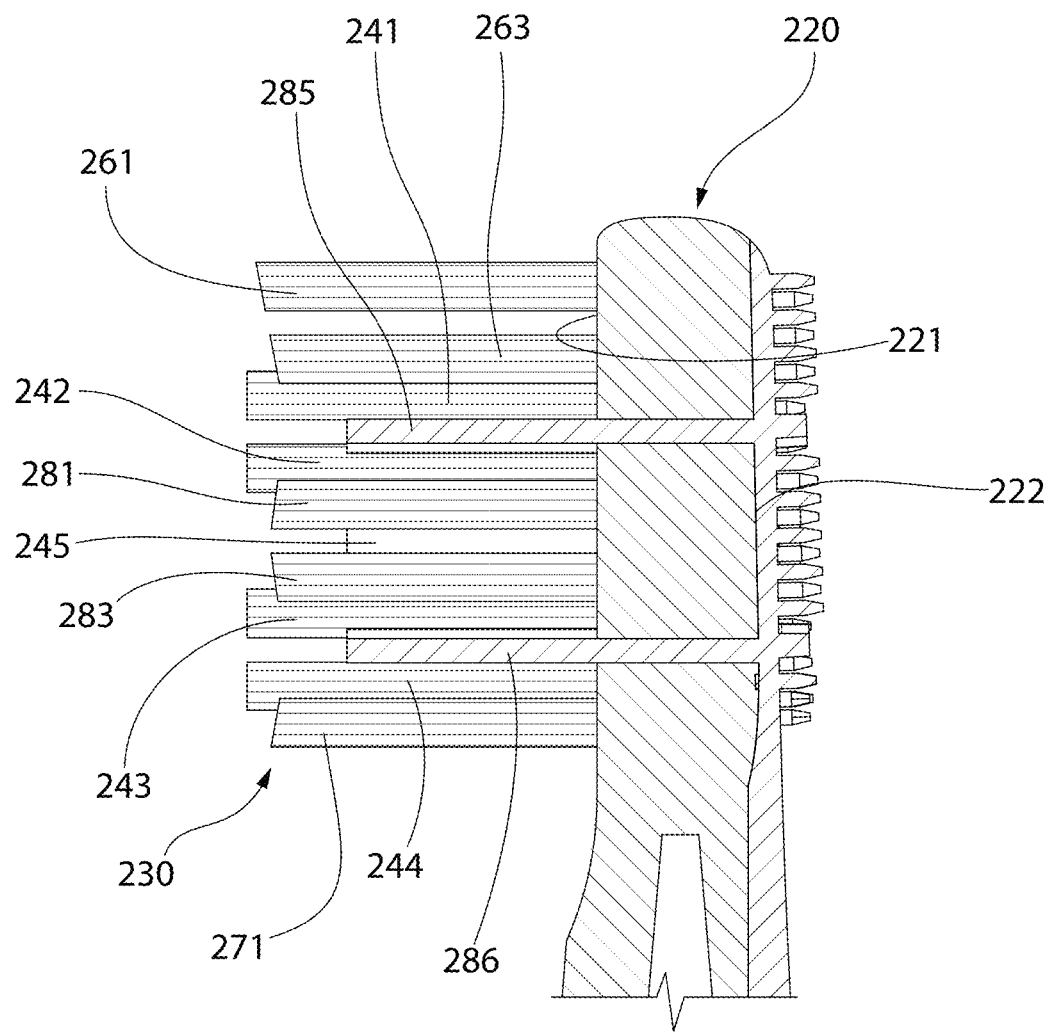
FIG. 13 is a cross-sectional view taken along line XIII-XIII of FIG. 11.

Referring to FIG. 9, an oral care implement 200 is illustrated in accordance with another embodiment of the present invention. The oral care implement 200 is similar to the oral care implement 100 except as described herein below. The description of the oral care implement 100 above generally applies to the oral care implement 200 described below except with regard to the differences specifically noted below. A similar numbering scheme will be used for the oral care implement 200 as with the oral care implement 100 except that the 200-series of numbers will be used.

The oral care implement 200 generally comprises a handle 210 and a head 220. The head 220 may be a refill head for an electric or powered toothbrush and as such the head 220 may be detachably coupled to the handle 210. Alternatively, the head 220 may be integrally formed with the handle 210 as a manual toothbrush or other oral care implement as described above.

The head 220 comprises a front surface 221 and an opposing rear surface 222. The head 220 extends from a proximal end 226 to a distal end 227 along a longitudinal axis B-B. Furthermore, the head 220 comprises a first peripheral side 228 and a second peripheral side 229, each of the first and second peripheral sides 228, 229 extending from the proximal end 226 to the distal end 227 and between the front and rear surfaces 221, 222 of the head 220. A plurality of tooth cleaning elements 230 extend from the front surface 221 of the head 220 and form a tooth cleaning element field.

The tooth cleaning element field comprises a first peripheral grouping of tooth cleaning elements 240, a second peripheral grouping of tooth cleaning elements 250, a distal grouping of tooth cleaning elements 260, a proximal grouping of tooth cleaning elements 270, and a central grouping of tooth cleaning elements 280. The general location and positioning of these groupings of tooth cleaning elements is the same as that which was described above with regard to FIGS. 1-8. However, the types of tooth cleaning elements within each grouping and the positioning of the different tooth cleaning within each grouping is different on the oral care implement 200 than on the oral care implement 100 described above.

In certain embodiments, with reference to the oral care implement 200 illustrated in FIGS. 9-13, the first and second peripheral groupings of tooth cleaning elements 240, 250 comprise a first type of tooth cleaning elements and a second type of tooth cleaning elements. Furthermore, the distal and proximal groupings of tooth cleaning elements 260, 270 comprise a third type of tooth cleaning elements. The central grouping of tooth cleaning elements 280 comprises a fourth type of tooth cleaning elements. The central grouping of tooth cleaning elements 280 may also comprise the second type of tooth cleaning elements. In certain embodiments, the first type of tooth cleaning elements may be a tapered bristle, the second type of tooth cleaning elements may be an elastomeric element, the third type of tooth cleaning element may be a single component end-rounded bristle, and the fourth type of tooth cleaning element may be also be a single component end-rounded bristle. In some embodiments the first and second peripheral groupings of tooth cleaning elements 240, 250 may consist of the first and second types of tooth cleaning elements, which may be the tapered bristles and the elastomeric elements, respectively. In some embodiments the distal and proximal groupings of tooth cleaning elements 260, 270 may consist of the third type of tooth cleaning elements, which may be single component end-rounded bristles. In some embodiments the central grouping of tooth cleaning elements 280 may consist of the second and fourth types of tooth cleaning elements, which may be the elastomeric elements and the single component end-rounded bristles, respectively.

The first peripheral grouping of tooth cleaning elements 240 comprises first, second, third, and fourth tufts of bristles 241, 242, 243, 244 and an elastomeric element 245. Each of the tufts of bristles 241-244 comprises the first type of bristles, which may be the tapered bristles 147 of FIGS. 4A and 4B. In this embodiment, the first and second tufts of bristles 241, 242 are positioned on one side of (above) the elastomeric element 245 and the third and fourth tufts of bristles 243, 244 are positioned on the opposite side of (below) the elastomeric element 245. Thus, the elastomeric element 245 is positioned longitudinally between the second and third tufts of bristles 242, 243. In certain embodiments, the first peripheral grouping of tooth cleaning 240 elements comprises the first and second types of tooth cleaning elements, the second type of tooth cleaning elements positioned between the first types of tooth cleaning elements.

The second peripheral grouping of tooth cleaning elements 250 comprises first, second, third, and fourth tufts of bristles 251, 252, 253, 254 and an elastomeric element 255. Each of the tufts of bristles 251-254 comprises the first type of bristles, which may be the tapered bristles 147 of FIGS. 4A and 4B. In this embodiment, the first and second tufts of bristles 251, 252 are positioned on one side of (above) the elastomeric element 255 and the third and fourth tufts of bristles 254, 254 are positioned on the opposite side of (below) the elastomeric element 255. Thus, the elastomeric element 255 is positioned longitudinally between the second and third tufts of bristles 252, 253. In certain embodiments, the second peripheral grouping of tooth cleaning 250 elements comprises the first and second types of tooth cleaning elements, the second type of tooth cleaning elements positioned between the first types of tooth cleaning elements.

The distal grouping of tooth cleaning elements 260 comprises the third type of tooth cleaning elements. In this embodiment, the third type of tooth cleaning elements is single component end-rounded bristles, such as the bristles 187 shown in FIGS. 6A and 6B. The distal grouping of tooth cleaning elements 260 comprises first, second, third, and fourth tufts of bristles 261, 262, 263, 264, each comprising the third type of bristles. In some embodiments the distal grouping of tooth cleaning elements 260 may consist of the third type of tooth cleaning element such that each of the first, second, third, and fourth tufts of bristles 261, 262, 263, 264 consists of the third type of tooth cleaning element or single component end-rounded bristles.

The proximal grouping of tooth cleaning elements 270 comprises the third type of tooth cleaning elements. In this embodiment, the third type of tooth cleaning elements is single component end-rounded bristles, such as the bristles 187 shown in FIGS. 6A and 6B. The distal grouping of tooth cleaning elements 260 comprises first and second tufts of bristles 271, 272, each comprising the third type of bristles. In some embodiments the proximal grouping of tooth cleaning elements 270 may consist of the third type of tooth cleaning element such that each of the first and second tufts of bristles 271, 272 consists of the third type of tooth cleaning element or single component end-rounded bristles.

The central grouping of tooth cleaning elements 280 comprises the second type of tooth cleaning element and the third type of tooth cleaning element. With reference to the exemplified embodiment, the central grouping of tooth cleaning elements 280 comprises first, second, third, and fourth tufts of bristles 281, 282, 283, 284, each comprising the third type of tooth cleaning element (i.e., single component end-rounded bristles). The central grouping of tooth cleaning elements 280 also comprises a first elastomeric element 285 and a second elastomeric element 286. In this embodiment, the first, second, third, and fourth tufts of bristles 281, 282, 283, 284 are positioned longitudinally between the first and second elastomeric elements 285, 286.

Furthermore, the first and second elastomeric elements 285, 286 are arcuate shaped elements having concave surfaces and convex surfaces. The concave surfaces of the first and second elastomeric elements 285, 286 face one another. The first and second elastomeric elements 285, 286 of the central grouping of tooth cleaning elements 280 and the elastomeric elements 245, 255 of the first and second peripheral groupings of tooth cleaning elements 240, 250 collectively form a loop that surrounds the first, second, third, and fourth tufts of bristles 281-284 of the central grouping of tooth cleaning elements 280.

In this embodiment, the tufts of bristles 281-284 of the central grouping of tooth cleaning elements 280 are taller than the first and second elastomeric elements 285, 286 of the central grouping of tooth cleaning elements 280. Furthermore, the tufts of bristles 241-244, 251-254 of the first and second peripheral groupings of tooth cleaning elements 240, 250 are taller than the elastomeric elements 245, 255 of the first and second peripheral groupings of tooth cleaning elements 240, 250. The tufts of bristles 241-244, 251-254 of the first and second peripheral groupings of tooth cleaning elements 240, 250 are also taller than the tufts of bristles 281-284 of the central grouping of tooth cleaning elements 280. The relative heights of the rest of the tooth cleaning elements 230 may be the same as that which was described above with regard to the oral care implement 100 and the tooth cleaning elements 130.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care implement comprising:
   a head extending along a longitudinal axis from a proximal end to a distal end, the head comprising a first peripheral side and a second peripheral side opposite the first peripheral side;
   a plurality of tooth cleaning elements extending from a front surface of the head, the plurality of tooth cleaning elements arranged in a tooth cleaning element field, the tooth cleaning element field comprising:
      a first peripheral grouping of tooth cleaning elements adjacent the first peripheral side of the head, the first peripheral grouping of tooth cleaning elements comprising a first type of tooth cleaning element and a second type of tooth cleaning element;
a distal grouping of tooth cleaning elements adjacent the distal end of the head, the distal grouping of tooth cleaning elements comprising a third type of tooth cleaning element;
a proximal grouping of tooth cleaning elements adjacent the proximal end of the head, the proximal grouping of tooth cleaning elements comprising the third type of tooth cleaning element; and
a central grouping of tooth cleaning elements located between the distal and proximal groupings of tooth cleaning elements, the central grouping of tooth cleaning elements comprising a fourth type of tooth cleaning element;
wherein the first type of tooth cleaning element is a tapered bristle, the second type of tooth cleaning element is an elastomeric element, the third type of tooth cleaning element is a spiral bristle, and the fourth type of tooth cleaning element is a single component end-rounded bristle.

2. The oral care implement according to claim 1 wherein the tooth cleaning element field further comprises a second peripheral grouping of tooth cleaning elements adjacent the second peripheral side of the head, the second peripheral grouping of tooth cleaning elements comprising the first and second types of tooth cleaning elements; and wherein the central grouping of tooth cleaning elements located between the first and second peripheral groupings of tooth cleaning elements.

3. The oral care implement according to claim 1 wherein each of the first and second peripheral groupings of tooth cleaning elements consists of the first and second types of tooth cleaning elements.

4. The oral care implement according to claim 1 wherein each of the first, second, third and fourth types of tooth cleaning elements are different from one another.

5. The oral care implement according to claim 1 wherein each of the proximal and distal groupings of tooth cleaning elements consists of the third type of tooth cleaning elements.

6. The oral care implement according to claim 1 wherein the central grouping of tooth cleaning elements further comprises the second type of tooth cleaning elements.

7. The oral care implement according to claim 6 wherein in the central grouping of tooth cleaning elements, the second type of cleaning elements are located between the fourth type of cleaning elements.

8. An oral care implement comprising:
a head extending along a longitudinal axis from a proximal end to a distal end, the head comprising a first peripheral side and a second peripheral side opposite the first peripheral side;
a plurality of tooth cleaning elements extending from a front surface of the head, the plurality of tooth cleaning elements arranged in a tooth cleaning element field, the tooth cleaning element field comprising:
a first peripheral grouping of tooth cleaning elements adjacent the first peripheral side of the head, the first peripheral grouping of tooth cleaning elements comprising tufts of tapered bristles and one or more elastomeric elements;
a distal grouping of tooth cleaning elements adjacent the distal end of the head, the distal grouping of tooth cleaning elements comprising tufts of spiral bristles; and
a proximal grouping of tooth cleaning elements adjacent the proximal end of the head, the proximal grouping of tooth cleaning elements comprising tufts of spiral bristles.

9. The oral care implement according to claim 8 further comprising a second peripheral grouping of tooth cleaning elements adjacent the second peripheral side of the head, the second peripheral grouping of tooth cleaning elements comprising tufts of tapered bristles and one or more elastomeric elements.

10. The oral care implement according to claim 9 further comprising a central grouping of tooth cleaning elements located between the first and second peripheral groupings of tooth cleaning elements and between the distal and proximal groupings of tooth cleaning elements, the central grouping of tooth cleaning elements comprising tufts of single component end-rounded bristles and one or more elastomeric elements.

11. The oral care implement according to claim 9 wherein each of the first and second peripheral groupings of tooth cleaning elements comprises at least two of the tufts of tapered bristles and at least two of the elastomeric elements, the at least two of the tufts of tapered bristles being located between the at least two elastomeric elements.

12. The oral care implement according to claim 9 wherein for each of the first and second peripheral groupings of tooth cleaning elements, the tapered bristles extend a greater distance from the front surface of the head than the elastomeric elements.

13. The oral care implement according to claim 9 wherein a transverse plane that is perpendicular to the longitudinal axis intersects one of the elastomeric elements of the first and second peripheral groupings of tooth cleaning elements and one of the spiral bristles of the distal grouping of tooth cleaning elements.

14. The oral care implement according to claim 9 wherein the spiral bristles of the proximal grouping of tooth cleaning elements have a first maximum height, the spiral bristles of the distal grouping of tooth cleaning elements have a second maximum height, the single component end-rounded bristles of the central grouping of tooth cleaning elements have a third maximum height, and the elastomeric elements of the central grouping of tooth cleaning elements have a fourth maximum height, and wherein the first and second maximum heights are greater than the third maximum height and the third maximum height is greater than the fourth maximum height.

15. The oral care implement according to claim 9 wherein the tufts of tapered bristles of the first and second peripheral groupings of tooth cleaning elements and the tufts of single component end-rounded bristles of the central grouping of tooth cleaning elements form a loop that surrounds the one or more elastomeric elements of the central grouping of tooth cleaning elements.

16. An oral care implement comprising:
a head extending along a longitudinal axis from a proximal end to a distal end, the head comprising a first peripheral side and a second peripheral side opposite the first peripheral side;
a plurality of tooth cleaning elements extending from a front surface of the head, the plurality of tooth cleaning elements arranged in a tooth cleaning element field, the tooth cleaning element field comprising:
a first peripheral grouping of tooth cleaning elements adjacent the first peripheral side of the head, the first peripheral grouping of tooth cleaning elements comprising tufts of tapered bristles and one or more elastomeric elements;

a distal grouping of tooth cleaning elements adjacent the distal end of the head, the distal grouping of tooth cleaning elements comprising tufts of single component end-rounded bristles; and a proximal grouping of tooth cleaning elements adjacent the proximal end of the head, the proximal grouping of tooth cleaning elements comprising tufts of single component end-rounded bristles.

17. The oral care implement according to claim 16 further comprising a second peripheral grouping of tooth cleaning elements adjacent the second peripheral side of the head, the second peripheral grouping of tooth cleaning elements comprising tufts of tapered bristles and one or more elastomeric elements.

\* \* \* \* \*